United States Patent [19]
Francis et al.

[11] Patent Number: 5,292,456
[45] Date of Patent: Mar. 8, 1994

[54] WASTE SITE RECLAMATION WITH RECOVERY OF RADIONUCLIDES AND METALS

[75] Inventors: Arokiasamy J. Francis, Middle Island; Cleveland J. Dodge, Wading River, both of N.Y.

[73] Assignee: Associated Universities, Inc., Washington, D.C.

[21] Appl. No.: 855,096

[22] Filed: Mar. 20, 1992

[51] Int. Cl.$^5$ ............................................. G21F 9/16
[52] U.S. Cl. .................................. 252/628; 210/611; 210/710; 210/748; 210/682
[58] Field of Search ............... 252/626, 628; 210/682, 210/611, 710, 748

[56] References Cited

U.S. PATENT DOCUMENTS

| | | | |
|---|---|---|---|
| 3,013,090 | 12/1961 | Pancer et al. | 134/3 |
| 3,047,434 | 7/1962 | Bulat | 134/1 |
| 3,297,580 | 1/1967 | Pitzer | 252/142 |
| 3,664,870 | 5/1972 | Oberhofer et al. | 134/3 |
| 4,320,093 | 3/1982 | Volesky et al. | 423/6 |
| 4,460,500 | 7/1984 | Hultgren | 252/628 |
| 4,468,461 | 8/1984 | Bopp | 435/253 |
| 4,530,763 | 7/1985 | Clyde et al. | 210/610 |
| 4,537,666 | 8/1985 | Murray et al. | 204/129.95 |
| 4,587,043 | 5/1986 | Murray et al. | 252/626 |
| 4,728,427 | 3/1988 | Revs et al. | 210/611 |
| 4,729,855 | 3/1988 | Murray et al. | 252/626 |
| 4,778,589 | 10/1988 | Reynolds | 208/252 |
| 4,789,463 | 12/1988 | Reynolds | 208/252 |
| 4,839,100 | 6/1989 | Goodall et al. | 252/626 |
| 4,943,357 | 7/1990 | Van Antwerp et al. | 204/157.15 |
| 4,973,201 | 11/1990 | Paul et al. | 405/264 |
| 5,047,152 | 9/1991 | Francis et al. | 210/611 |

OTHER PUBLICATIONS

Rajan et al., Inorganic Chemistry, vol. 4, No. 4, 402–469 (1965).
Nunes et al., Inorganic Chemica Acta, vol. 129, 283–287 (1987).
"Stability Constants of Metal-Ion Complexes" Supplement No. 1, The Chemical Society, 411–415 (1971).
M. E. Holland, "Use of Citric Acid for Large Parts Decontamination", Chemical Abstracts, vol. 93, 1980, pp. 326.
Brynhildsen, et al., "Effects of Cadmium, Copper, Magnesium, and Zinc on the Decomposition of Citrate by a Klebsiella sp.", Applied and Environmental Microbiology, Jun. 1989, pp. 1375–1379.
Adams, et al., "The Formation and Photochemical Oxidation of Uranium (IV) Citrate Complexes", J. Chem. Soc., 1960, pp. 4846–4850.
Madsen, et al., "Effects of Chemical Speciation on the Mineralization of Organic Compounds by Microorganisms", Applied and Environmental Microbiology, Aug. 1985, pp. 342–349.
Nishita, et al., "Effect of Inorganic and Organic Compounds on the Extractability of $^{239}$Pu from an Artificially Contaminated Soil", J. Environ. Qual., vol. 6, No. 4, 1977, pp. 451–455.
A. J. Francis, "Characteristics of Nuclear and Fossil Energy Wastes", Experentia, 46, 1990, Birkhauser Verlag, CH–4010, Basel, Switzerland.

(List continued on next page.)

Primary Examiner—Donald P. Walsh
Assistant Examiner—Nigoclan T. Mai
Attorney, Agent, or Firm—Margaret C. Bogosian

[57] ABSTRACT

A method for decontaminating radionuclides and other toxic metal-contaminated soil, sediment, sludge and aquatic milieus involves treating the contaminated material with a hydroxycarboxylic complexing agent in a solution. The treatment solution is then treated with a Pseudomonas fluorescens ATCC No. 55241 and subjected to photolysis to degrade the complex and recover the radionuclides and metals in a concentrated form through precipitation or incorporation into biomass.

13 Claims, 6 Drawing Sheets

OTHER PUBLICATIONS

Francis, et al., "Microbial Transformations of Uranium in Wastes", Radiochimica Acta/52/53, pp. 311–316, 1991.

A. J. Francis, "Microbial Dissolution and Stabilization of Toxic Metals and Radionuclides in Mixed Wastes", Experientia 46, 1990, Birkhauser Verlag, CH-4010, Basel, Switzerland.

Raghaven, et al., "Cleaning Excavated Soil Using Extraction Agents: A State-of-the-art Review. Final Report, Jun. 1985–1989", Energy Research Abstracts, vol. 15, No. 1, Jan. 15, 1990, Office of Scientific & Technical Information, DOE.

Kochen et al., "Americium and Plutonium Removal from Contaminated Soil", Energy Research Abstracts, vol. 10, No. 17, Sep. 15, 1985, Office of Scientific & Technical Information, DOE.

Campbell, et al., "In situ Vitrifi-ation of a Mixed Radioactive and Hazardous Waste Site", Energy Research Abstracts, vol. 16, No. 3, Mar. 1991, Office of Scientific and Technical Information, DOE.

Madic, et al., "Extraction of Metal Ions by Neutral B-diphosphoramides", Energy Research Abstracts, vol. 16, No. 2, Feb. 1991, Office of Scientific and Technical Information, DOE.

Kim, et al., "Immobilization of Radioactive Strontium in Contaminated Soils by Phosphate Treatment", Energy Research Abstracts, vol. 16, No. 1, Jan. 1991, Office of Scientific and Technical Information, DOE.

C. W. Francis, "An Assessment of Soil Washing to Remove Uranium and Mercury from Oak Ridge Soils", The Department of Energy's Soil Washing Workshop, Aug. 28–29, 1990.

(A) CITRIC ACID (B) BIDENTATE COMPLEX (C) TRIDENTATE COMPLEX (D) BINUCLEAR COMPLEX

WASTE SITE RECLAMATION WITH RECOVERY OF RADIONUCLIDES AND METALS

The U.S. government has certain rights in this invention pursuant to Contract Number DE-AC02-76CH00016 between the U.S. Department of Energy and Associated Universities, Inc.

BACKGROUND OF THE INVENTION

This invention relates to a process for removing metals from contaminated materials such as soils, sediments, sludges, and aquatic environments, so that the contaminated material may be reclaimed.

Radionuclides and toxic metals are present in certain wastes, particularly in waste disposal sites such as those of the Department of Energy. These contaminants may also leach from the waste sites and cause environmental contamination. For decontamination of waste material, both the metal and radionuclide contaminants must be removed from the contaminated site. This presents the problems of removing radionuclides and metals from the soil or water so that the site can be returned to a useful condition. It would be desirable and beneficial to the environment to provide a comprehensive method for the removal of toxic metals and radionuclides from contaminated sites with reclamation of the soil and water.

Previous large scale methods devised to deal with the problem of contaminated soil have utilized caustic reagents such as hot sulfuric or hydrochloric acids and oxidizing agents such as sodium hypochlorite to extract metals from soil. While these methods can remove contaminants, they also cause irreparable damage to the soil. Prior art methods generate secondary waste streams which create additional hazardous waste disposal problems. Various soil washing methods were discussed by C. W. Francis in a presentation, "An Assessment of Soil Washing to Remove Uranium and Mercury From Oak Ridge Soils", at the Department of Energy's Soil Washing Workshop, Aug. 28-29, 1990. See also, B. E. Campbell and S. S. Koegler, "In Situ Vitrification of a Mixed Radioactive and Hazardous Waste Site", Energy Research Abstracts 7186 (March 1991) describing the use of electrodes inserted into the ground to vitrify a waste site; C. Madic et al., "Extraction of Metal Ions by Neutral B-Diphosphoramides", Energy Research Abstracts 3636 (February 1991) describing the use of bidentate phosphoramides enhanced by nitric acid to extract metal ions such as lanthanides, uranyl and the transuranium elements AM(III) and Pu(IV); K. H. Kim, et al., "Immobilization of Radioactive Strontium in Contaminated Soils by Phosphate Treatment", Energy Research Abstracts 1993 (January 1991) describing coprecipitation of strontium 90 with Ca-, Al- and Fe-phosphate in contaminated soils; R. Raghaven, et al. "Cleaning Excavated Soil Using Extraction Agents: A State-of-the-Art Review. Final Report June 1985-January 1989", Energy Research Abstracts 5106 (Jan. 15, 1990) describing three generic types of extractive treatments for cleaning excavated soils: water washing augmented with a basic or surfactant agent to remove organics and with an acidic or chelating agent to remove organics and heavy metals, organics-solvent washing to remove hydrophobic organics and polychlorinated biphenyls, and air or steam stripping to remove volatile organics; R. L. Kochen and J. D. Navratil, "Americium and Plutonium Removal From Contaminated Soil", Energy Research Abstract 36247 (Sep. 15, 1985) describing reducing the volume of contaminated soils by wet-screening, attrition scrubbing, wet-screening with additives, and fixation by conversion to glass.

Various specialized kinds of metal removal from soil have been known in the art. For example, a method for solubilizing a metal-containing precipitate has been described in U.S. Pat. No. 4,973,201 to Paul et al.. This patent describes a method for solubilizing precipitated alkaline earth metal sulfate scale in contaminated earth by contacting the earth with a polyaminocarboxylic acid chelating agent (ETDA or DTPA) and an oxalate ion synergist and leaching the solubilized precipitate from the earth with water. To dispose of the dissolved sulfates, the leachate is said to be treated by chemical methods or returned to a subterranean formation.

In a study directed to devising a method to correlate with Pu uptake by plants in contaminated soils, the extraction of plutonium from contaminated soil with inorganic and organic compounds including citrate was described by H. Nishita et al., "Effect of Inorganic and Organic Compounds on the Extractability of $^{239}$pU from an Artificially Contaminated Soil", J. Environ. Qual. 6, 451-455 (1977).

Radioactive contaminated components of nuclear reactors have been decontaminated using citric acid or citrates as described, for example, in U.S. Pat. Nos. 4,839,100, 4,729,855, 4,460,500, 4,587,043, 4,537,666, 3,664,870 and 3,103,909. In these patents, metal recovery methods involve ion exchange columns, porous DC electrodes or combusting the organics.

U.S. Pat. No. 4,943,357 describes the use of ultra violet light with a wavelength less than 210 nm using a mercury lamp for photodegradation of metallic chelate complexes, particularly nickel ethylenediaminetetraacetic acid (EDTA) from nickel plating baths. An article by A. Adams and T. D. Smith, "The Formation and Photochemical Oxidation of Uranium(IV) Citrate Complexes", J. Chem. Soc. 4, 4846-4850 (1960) describes photochemical oxidation of uranium(IV) chelate of citric acid using a tungsten filament lamp.

The effects of chemical speciation on microbial mineralization of metal organic complexes by sewage microorganisms *Pseudomonas alcaligenes, Pseudomonas pseudoalcaligenes* and *Listeria* sp. is described by E. L. Madsen and M. Alexander, "Effects of Chemical Speciation on the Mineralization of Organic Compounds by Microorganisms", Applied and Environmental Microbiology 50, 342-349 (1985). L. Brynhildsen and T. Rosswall, "Effects of Copper, Magnesium, and Zinc on the Decomposition of Citrate by a *Klebsiella* sp.", Applied and Environmental Microbiology 55, 1375-1379 (1989) describe the effects of $Cd^{2+}$, $Cu^{2+}$, $Mg^{2+}$ and $Zn^{2+}$ on the decomposition of citric acid by a *Klebsiella* sp. also isolated from sewage. These researchers found that some metals may render citric acid resistant to bacterial degradation.

Many chelates have been shown to be either poorly biodegraded by microorganisms under aerobic conditions or to undergo little biodegradation under anaerobic conditions. See, e.g. Francis, A. J., "Microbial Dissolution and Stabilization of Toxic Metals and Radionuclides in Mixed Wastes", Experientia 46, 840-849 (1990); and A. J. Francis et al., "Microbial Transformations of Uranium in Wastes", Radiochemica Acta 52/53, 311-316 (1991).

Various isolated concepts have been described in the art. But the problem of providing thorough waste site decontamination heretofore has not been solved. Furthermore, nothing has suggested a total method for reclaiming radionuclide or toxic metal-contaminated soil, sediments, sludges and water with recovery of the contaminating metals to reduce toxic waste, and with restoration of undamaged soil or water.

Accordingly, it is an object of the invention to provide a comprehensive method which can remove even recalcitrant radionuclides from contaminated soil, sediments, sludges and water.

DEPOSIT

The bacterium utilized in the present invention is a citrate-degrading *Pseudomonas fluorescens* which has been deposited in the American Type Culture Collection (Rockville, Md.) in accordance with the Manual of Patent Examining Procedure and prior to the filing of this application. This deposit assures the permanence and availability of the bacterium for at least the life of the patent. This *Pseudomonas fluorescens* has been accorded deposit number ATCC No. 55241.

SUMMARY OF THE INVENTION

The invention is a method for decontaminating radionuclide and/or metal-contaminated waste material such as soil, sediment, sludge, and aquatic environments. The contaminated waste material is contacted with a complexing agent comprising a hydroxycarboxylic acid, hydroxycarboxylic salt or mixture thereof in a solution to yield a radionuclide and/or metal complex containing solution. The metal complex containing solution and particulate matter of the waste material are separated from each other, and the solution is treated with a bacterial culture containing *Pseudomonas fluorescens* ATCC No. 55241. The solution is exposed to light for a photodegradation effect before, after, or concurrent with the bacterial contacting. Contaminating radionuclides and/or metals are concentrated for recovery through polymer formation, precipitation and/or incorporation into biomass (biosorption).

Advantageously, the method allows reclamation of contaminated soils, sediments and sludges while avoiding soil damage. The method also results in a dramatic reduction of waste volume by selectively removing toxic and non-toxic components. Furthermore, the combination of photodegradation and biodegradation allows removal of many different metals having different properties. Also advantageously, the method is ecologically beneficial.

For a better understanding of the present invention, together with other and further objects, reference is made to the following description, taken together with the accompanying drawings, and its scope will be pointed out in the appended claims.

DETAILED DESCRIPTION OF THE INVENTION

Figure 1:
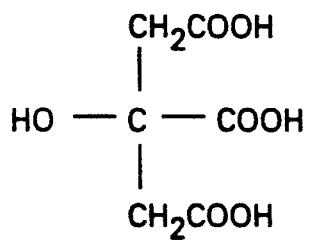
FIG. 1 is an illustration of the types of complexes formed by citric acid with different metals.
Figure 1:
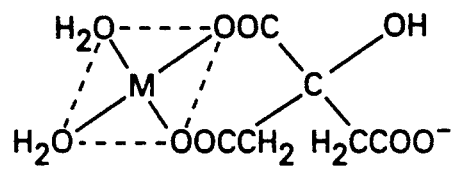
Figure 1:
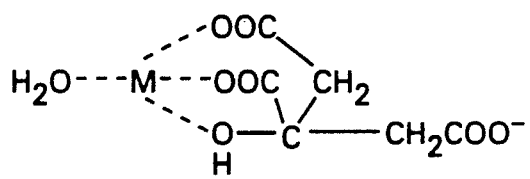
Figure 1:
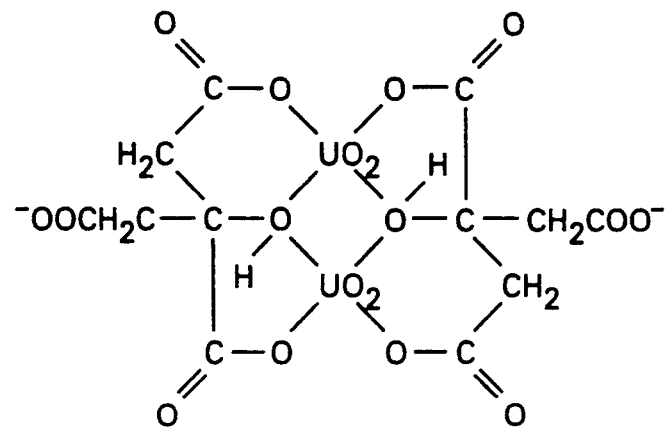

The invention provides a comprehensive method for removing metals such as radionuclides and toxic metals from contaminated soils, sludges, sediments and aqueous environments. Soil may be considered to be the upper layer of earth. Sediment includes soil and organic material deposited, for example, by wind, water or glaciers. Sludge is residual material created from a treatment process.

Radionuclides and toxic metals are present in industrial and governmental agency wastes and have been reported to migrate from waste disposal sites. The process leading to restoration of contaminated sites includes the use of an organic complexing agent to complex these contaminating metals. This process removes contaminating metals through complex formation and dissolution. Microbial degradation and photolytic degradation are used to recover the metal. Microbial and photolytic treatment of organic complexing agents and complexes results in the destruction of the complexing agent or organic portion of the complex to carbon dioxide or other innocuous materials with precipitation and/or biomass stabilization of the released radionuclides and toxic metals.

Radionuclides and metals present in nuclear and fossil energy wastes have been described by inventor herein, A. J. Francis, "Characteristics of Nuclear and Fossil Energy Wastes", Experientia 46, 794–796 (1990). These wastes include the categories of high-level radioactive, transuranic, low-level radioactive, uranium mining and processing, coal mining and processing, coal combustion and coal conversion wastes.

The invention is especially concerned with reclamation of disposal sites for transuranic, low-level radioactive, uranium, coal and coal combustion wastes. Of particular concern are sites contaminated with uranium. The sludge and sediment wastes from a uranium processing facility contain high levels of uranium and toxic metals. Uranium and toxic metals in this type of material may be associated with minerals to a varying degree as carbonate, iron oxide, organic and inert fractions.

A method has been devised to complex metal in wastes using a hydroxycarboxylic acid or salt with degradation of the organic to allow recovery of contaminating metals for recycling or appropriate disposal.

It was necessary to solve a number of problems in devising this method. Sufficient hydroxycarboxylic acid must be used to complex the contaminating metals. If insufficient hydroxycarboxylic acid is used, an unacceptable amount of metal will remain in the waste. Therefore, when a large amount of metal is present, or when it is desirable to insure essentially complete decontamination, a fairly substantial amount of the hydroxycarboxylic acid is used. However, the use of a substantial amount of hydroxcarboxylic acid in itself presents a potential problem through interference by the organic acid in metal recovery. Therefore it is sometimes necessary to remove excess hydroxycarboxylic acid after the extraction process by degrading it so that the metal can be recovered. Aside from the problem of degrading excess hydroxycarboxylic acid, it is also necessary to be able to efficiently degrade diverse types of metal-citrate complexes to recover the metals. In some cases, essentially one type of metal may be present, but more commonly, many different types of contaminating metals may be coexistent in the waste. Since different metals are complexed in different ways, the method of removing metals from metal-citrate complex must be capable of degrading complexes of different types of metals. A method has been devised using a combination of metal complexation, biodegradation and photodegradation to solve the problems of removing excess citric acid and degrading diverse types of metal-citrate complexes.

A hydroxycarboxylic acid particularly useful in the invention is citric acid. Citric acid treatment of soil results in little loss in the physical and chemical properties of soils; thus the soil can be reused. This is in contrast to the damaging caustic or acid treatments previously used in soil washing. At the proper pH in solution, citric acid's hydroxyl and carboxylic acid groups act as multidentate ligands forming complexes or chelates with metal ions. The citric acid is preferably in aqueous solution. A useful citric acid and/or salt treating solution has a citrate concentration of from 0.01 to 1.0M, preferably 0.10 to 0.60M. Commercially available salts of citric acid include calcium citrate, potassium citrate and sodium citrate. Citric acid or salt is added to a final concentration of from about 0.01M to about 1.0M with from about 0.1M to about 0.6M preferred. The citrate solution is preferably added in a concentration in excess of the concentration of metals to be removed. It is important that a bacterial culture be capable of degrading citric acid and metal citrate complexes.

Citric acid forms bidentate, tridentate, and polynuclear complexes with metals. The following metals are extracted by citric acid: Ag, Al, Am, Au, Ba, Be, Ca, Cd, Ce, Cm, Co, Cr, Cs, Cu, Dy, Er, Eu, Fe, Ga, Gd, Hf, Hg, Ho, In, Ir, K, La, Li, Lu, Mg, Mn, Mo, Na, Nb, Nd, Ni, Np, Os, Pa, Pb, Pd, Pm, Pr, Pt, Pu, Rb, Re, Ru, Sb, Sc, Sm, Sn, Sr, Ta, Tb, Tc, Th, Ti, Tl, Tm, U, V, W, Y, Yb, Zn, Zr. These metals comprise all of Groups 1A to 12 as well as significant portions of Groups 13-15, all of the lanthanides and one half of the antinides. The efficiency of extraction and the ability to extract these metals from specific types of waste depends on the nature of the metal association in the waste. Wastes which are preferably treated by the method of the invention contain those metals which form tridentate and polynuclear complexes: Th, Pa, U, Np, Pu, Am, and Cm; all of the transition metals from Group 3 to 12, as well as Pb are extracted by citric acid. Most preferably treated because of the serious contamination problems which they cause, are Th, Pa, U, Np, Pu, Am, and Cm; toxic metals Be, Cr, Mn, Co, Ni, Cu, Zn, Cd, and Pb all of which may be extracted by citric acid.

A citric acid degrading bacteria isolated from a low-level radioactive waste disposal site rapidly degraded citrate. This culture was determined to be a *Pseudomonas fluorescens*. The bacteria metabolizes 0.52 mM citric acid in defined medium in less than fifteen hours at a rate of 57 $\mu$moles/hour.

Bacterial contacting with the citric acid extract may be in a batch or continuous process. Either process may be carried out in any suitable enclosure. A continuous process may be carried out such that treated solution is periodically removed while untreated solution is periodically added. The solution is contacted with the bacterial culture under aerobic conditions, that is, in the presence of oxygen and under conditions to achieve a steady state population density. Population density varies from about $2 \times 10^6$ to $2 \times 10^9$ cells/mL of solution and is preferably about $2 \times 10^7$ to $2 \times 10^8$ cells/mL of solution. Contacting is at a temperature of about 15° C. to about 37° C., preferably from about 18° C. to about 32° C., and most preferably from about 20° C. to about 30° C. The initial pH is about 4-8, preferably 6-7. The bacteria metabolizes the citrate, in a contacting time of, for example, about 24 hours to about 5 days. Conditions for contacting are sufficient to cause a breakdown of the citrate.

Microbial treatment of the metal-organic complex results in the destruction of the organic portion of the complex to carbon dioxide or other innocuous product(s) and at the same time, stabilizes the released radionuclides and toxic metals.

Biodegradation of the metal citrate complex depends upon the nature of the complex between metal and citrate. These complexes may be bidentate, tridentate or binuclear as shown in FIG. 1. While it is not intended to be bound by theory, it is believed that some metals such as calcium, iron(III) and nickel form mononuclear bidentate complexes with two of the three carboxylic acid groups of citrate. These bidentate complexes are readily biodegraded. Other elements such as cadmium, copper, iron(II) and lead form mononuclear tridentate complexes involving two carboxylic acid groups as well as the alcoholic hydroxyl group of the citrate, a more recalcitrant complex. However, if Fe(II) becomes oxidized to Fe(III), it is biodegraded. Uranium forms a binuclear complex with two citric acid molecules involving four carboxylic acid groups and two alcoholic hydroxyl groups thus increasing the structural stability and recalcitrance of the complex. Complexes of other metals, such as cadmium, copper and lead, can be degraded cometabolically through the addition of other carbon sources such as glucose. During cometabolic degradation, the complex structure is altered due to changes in the pH of the growth medium, releasing the metal from the complex resulting in the precipitation or biosorption of the metals. More recalcitrant complexes such as those of radionuclide citrate complex, e.g., that of uranium, can be effectively degraded by photolysis.

Photolysis involves the decomposition or dissociation of a molecule as a result of the absorption of light. When the solution containing citrate-metal complex is subjected to light, photochemical degradation (hereinafter "photodegradation") of the citrate occurs and the metal is precipitated. The effective light for photodegradation may be in the visible spectrum and/or the ultraviolet spectrum. Visible light may be described as electromagnetic radiation capable of inducing visual sensation, with wavelengths between about 400 nm and about 800 nm, preferably 400 to 450 nm. Also useful is ultraviolet light in a wavelength range from about 400 nm to 10 nm, i.e. between the visible and x-ray regions of the spectrum. Near UV is 400–300 nm; middle UV is 300–200 nm; and extreme of 200–190 nm. A particularly useful source of visible or ultraviolet light for practical reasons, is sunlight.

For photodegradation, the pH of the solution is from about 2 to about 8, preferably from about 3 to about 4. The citrate-metal complex is subjected to light for a time of at least about 12 hours, preferably at least 72 hours. Time of photodegradation is related to whether the step is carried out under aerobic or anaerobic conditions. The photodegradation takes place more quickly and completely under aerobic conditions so that essentially total degradation of iron and uranium complexes may occur in less than about 75 hours, or preferably in a time of from about 5 hours to about 70 hours. Although photodegradation occurs under either aerobic or anaerobic conditions, it is more efficient under aerobic conditions. Addition of ferric iron also enhances the photodegradation of excess uncomplexed citric acid.

The temperature at which photodegradation is undertaken is not critical and is limited for practical reasons only by the freezing point or boiling point of the solution.

In a preferred embodiment, the process involves contacting the contaminated material with citric acid or citrate in solution to complex contaminating radionuclides and metals and thus extract them. After contact with citrate in solution, the particulate segment of the contacted material, e.g., particles of the soil, sediment or sludge are separated out leaving an effluent solution containing radionuclide/metal-citrate complex. Particle separation may be by known means such as sedimentation, filtration, centrifugation or combinations of separation methods.

The metal is removed from the metal-citrate complex in the solution by degrading the citrate. This degradation may be attained using a photolytic effect of visible light on citrate and/or through bacterial biodegradation using a strain of Pseudomonas fluorescens ATCC No. 55241. For thorough degradation of mixed metal complexes, a combination of biodegradation and photolysis is used. Using biodegradation, the metal becomes precipitated or incorporated into biomass; and using photodegradation, the metal becomes polymerized and precipitates out so that the metal can be recovered. The treated material is left undamaged.

The method for recovery of the metal can be varied according to waste type and type of metals being removed and can involve the following process sequences:

I. The citric acid extract containing radionuclide/metal complexes is first subjected to biodegradation followed by photodegradation to remove excess citric acid and metal complexes.
   Citric acid→Biodegradation→Photodegradation→Recovery of metal II. The citric acid extract containing radionuclide/metal complexes is first subjected to photodegradation followed by biodegradation.
   Citric acid extract→Photodegradation→Biodegradation→Recovery of metal III. Alternatively, citric acid extract containing radionuclide/metal complexes is subjected to biological and photolytic degradation simultaneously.
   Citric acid extract→Biodegradation/Photodegradation→Recovery of metal The precipitated toxic metals and radionuclides resulting from any of the above processes I–III are then separated from the effluent and recovered. The effluent meets environmental standards and can be discharged.

In a specific embodiment, toxic metal-containing waste from a uranium processing facility is treated. The metal contaminants include uranium, cadmium, cobalt, copper, iron, lead, nickel, and zinc. In a suitable container, the waste is mixed with an aqueous solution of citric acid so that the mixture has a citric acid concentration ratio of about 2 citric acid:1 metal. The mixture is agitated about 5 hours at ambient temperature to allow complexation of the metals by citric acid. The mixture is also allowed to stand until the particulate matter of the waste settles to the bottom leaving an aqueous solution of metal-citrate complex at the top. The solution is removed and treated to degrade the metal citrate complex. The reclaimed soil at the bottom may be returned to productive use. After the particulate matter has been removed from the solution, the pH of the solution is adjusted to about pH 6–7 if necessary, amended with nutrients $NH_4Cl$, 1.0 g/l, $K_2HPO_4$, 1.0 g/l, and $KH_2PO_4$, 1.0 g/l and subjected to biodegradation. The citric acid extract is inoculated with a culture of Pseudomonas fluorescens, ATCC No. 55241 in an amount of about 1–4% by volume. The bacterium is grown in the following medium: citric acid 2 g; $NH_4Cl$, 1.0 g, $K_2HPO_4$, 1.0 g; $KH_2PO_4$, 1.0 g; NaCl, 4.0 g; $MgSO_4$, 0.2 g; deionized $H_2O$ 1000 ml and pH 6.5. The inoculated solution is allowed to stand or agitated at a temperature of about 20°–30° C. for about 1 to 3 days. During this time, the excess citric acid and metal citrate complexes of such as nickel, Fe(III), and calcium are degraded allowing the metals to hydrolyze to the bottom or react with the bacterial biomass. The biomass along with the metals are removed by filtration. The remaining solution containing uranium citrate complex is subjected to photodegradation after pH adjustment (3–5) if necessary. In a suitable container such as a tank or pond, the solution is exposed to sunlight for about a week. During this time, citrate complexes of uranium(VI) and other metals such as Fe(III) are photodegraded and the uranium(VI) and other released metals precipitate out as a polymeric material and settle to the bottom. The remaining solution meets government standards for non-hazardous waste and may be discharged in a conventional manner. At the same time, the initially contaminated soil has been reclaimed, and the toxic contaminating metals have been concentrated for environmentally-sound disposition.

If required, additional treatment with a supplemental carbon source such as glucose (0.5 to 5.0 g/l) can result in the degradation of resistant complexes such as Cu, Cd and Pb.

Photoreactive compound is a metal ion which is added to enhance citrate degradation. Examples of photoreactive compounds are salts which include Fe(III). Additional photoreactive compound may also be added to aid in the degradation of resistant radioactive elements.

In another embodiment, the photodegradation may be carried out before biodegradation. In still another embodiment, the aqueous metal complex solution may be inoculated with bacteria and allowed to stand in the presence of light so that photodegradation and biodegradation occur simultaneously.

The following non-limiting examples illustrate the invention.

Culture Medium

A medium was developed in accordance with equilibrium calculations using a computer program so that the cation complex to be studied was the predominant species.

The medium consisted of the following ingredients (per liter): $NH_4Cl$, 35.8 mg; $CaCl_2.2H_2O$, 2.75 mg; $MgCl_2.6H_2O$, 6.25 mg; PIPES buffer (disodium salt, Sigma Chemical Co., St. Louis, Mo.), 1.47 mg; glycerolphosphate, 1.74 mg; $FeSO_4.7H_2O$, 1.49 mg; $MnSO_4.H_2O$, 1.155 mg; $CuCl_2.2H_2O$, 0.101 mg; $CuCl_2.2H_2O$, 0.101 mg; $Na_2MoO_4.2H_2O$, 0.0945 mg; $ZnSO_4.H_2O$, 0.103 mg; $CoCl_2.6H_2O$, 0.151 mg; citric acid (anhydrous, Sigma Cell Culture Reagent, St. Louis, Mo.), 100 mg. The ionic strength of the medium was adjusted to 0.1M by the addition of 7.4 g KCl. The pH was adjusted to 6.2 with potassium hydroxide. The PIPES buffer and glycerolphosphate were used to prevent the precipitation of metals.

Citrate Analysis

Degradation of citrate was monitored by high pressure liquid chromatography (HPLC, Spectra Physics) using a uv-vis detector at 210 nm after filtration through a 0.22 μm Millex filter.

Isolation of Citrate Degrading Bacteria

A citric acid degrading bacterial culture was isolated by enrichment technique from a low-level radioactive waste disposal site at West Valley, N.Y. A biologically pure culture was identified as a *Pseudomonas fluorescens* and has been assigned deposit number ATCC No. 55241.

Preparation of Metal Citrate Complexes

Citric acid solution was standardized by dissolving 2.5 grams citric acid in one liter deionized water (13.0 mM) and titrated with an aliquot of 0.10N NAOH prepared from Acculute (Anachemia Chemicals, NY). Metal solutions (13.0 mM) were freshly prepared in deionized water using the following compounds: $CaCl_2.2H_2O$, MCB ACS reagent; $Cd(NO_3)_2.4H_2O$, Alfa Products; $CuCl_2.2H_2O$, Mallinckrodt AR grade; $FeSO_4.7H_2O$, Mallinckrodt AR grade; $Fe(NO_3)_3.9H_2O$, Mallinckrodt AR grade; $Ni(NO_3)_2.6H_2O$, Alfa Products; $Pb(NO_3)_2$, Mallinckrodt AR grade; $UO_2(NO_3)_2.6H_2O$, BDH Chemicals (Analar), Poole, England. The concentrations of the metals in solution were determined using atomic absorption spectrophotometry. Uranium was analyzed by a colorimetric procedure. The 1:1 metal citrate complexes (except for Pb) were prepared by slowly adding equimolar amounts of citrate and then metal solution to a sterile acid washed beaker. The solution was continuously stirred and diluted with deionized water to give a final concentration of 0.52 mM metal citrate complex. The pH was adjusted to 6.2 with 1.0N NaOH. Due to the low solubility of lead citrate in the undiluted complex, the lead and citric acid were added separately directly to the growth medium in the examples involving the bacterial culture medium.

EXAMPLE 1

Bacterial Degradation of Metal Citrate Complexes

The ability of the bacterial culture ATCC No. 55241 to degrade equimolar 1:1 metal-citrate complexes of $Ca^{2+}$, $Cd^{2+}$, $Cu^{2+}$, $Fe^{2+}$, $Fe^{3+}$, $Ni^{2+}$, $Pb^{2+}$, or $UO_2^{2+}$ was tested under aerobic conditions. The treatments consisted of (i) 0.52 mM metal citrate complex inoculated with the bacteria, and (ii) 0.52 mM metal citrate complex (uninoculated, sterile control). To 180 ml of autoclaved medium in a 500 ml acid washed erlenmeyer flask, filter sterilized, metal citrate complex (after passing through a 0.22 μm Millex filter) was added aseptically to the medium. The pH of the final medium containing the metal complex was adjusted to 6.2 by adding a predetermined amount of filter sterilized base or acid to each flask. The samples were inoculated with 1 ml of early logarithmic growth phase bacterial culture and incubated in the dark on a reciprocating shaker at 26°±1° C. Samples were taken periodically and analyzed for pH, metal, and citrate.

Figure 2:
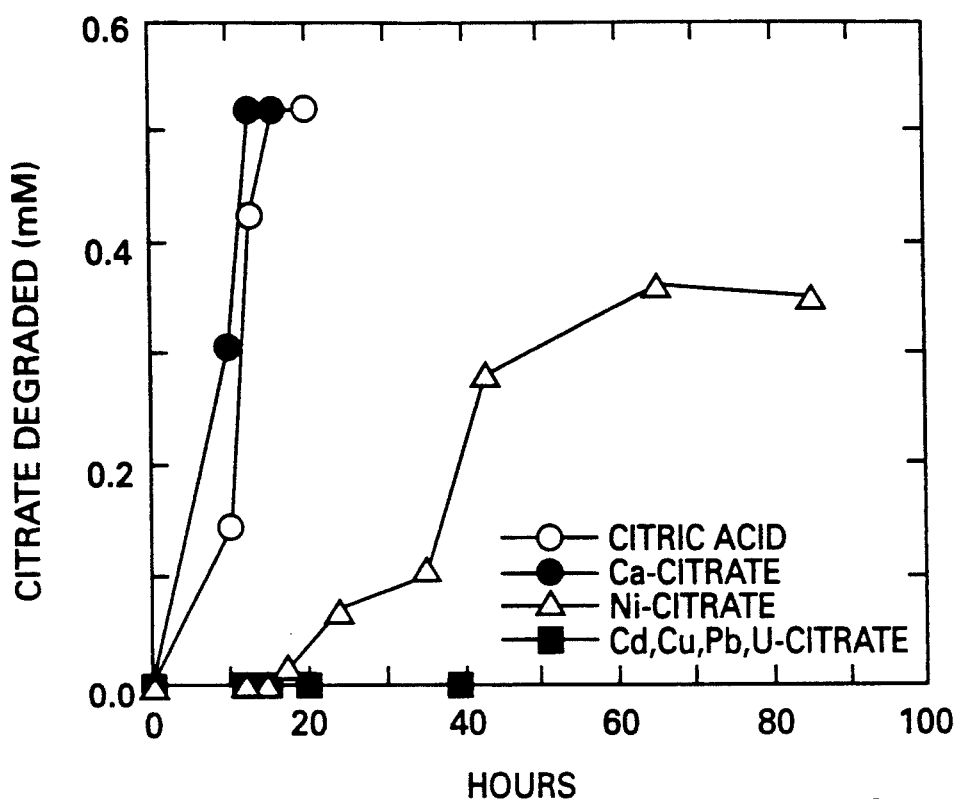
FIG. 2 is a graph of bacterial degradation of citrate complexes of calcium, nickel, cadmium, copper, lead and uranium.
Figure 3:
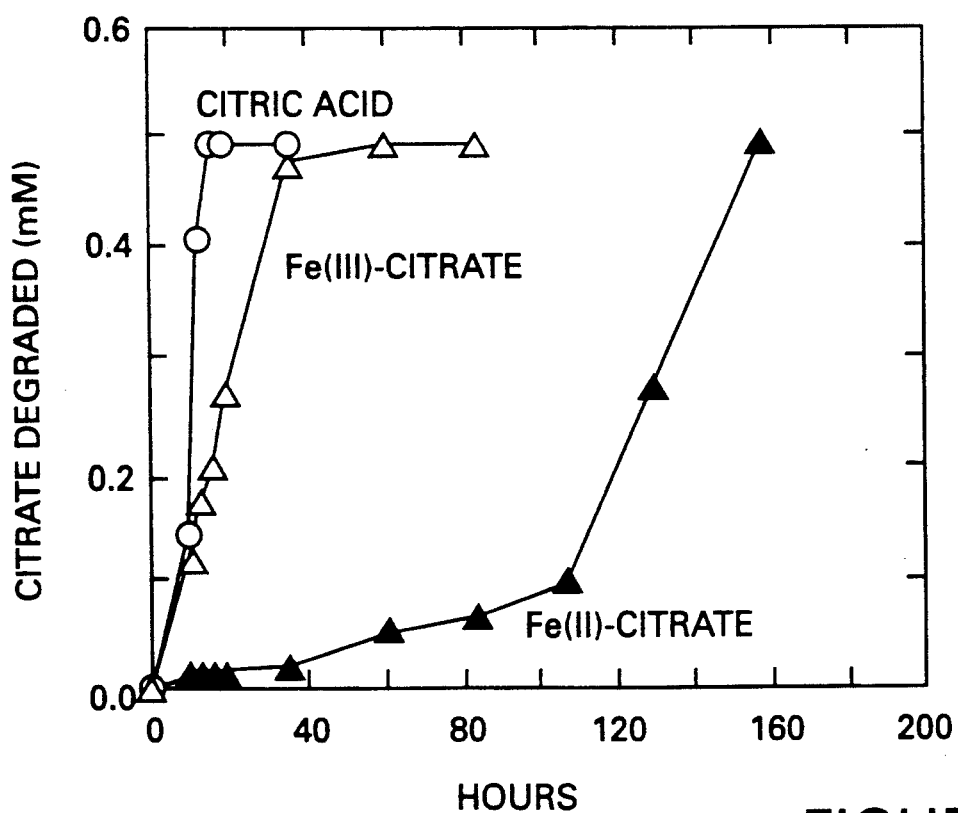
FIG. 3 is a graph of bacterial degradation of iron citrate complexes.

The results of the bacterial degradation of citric acid, Ca—, Ni—, Cd—, Cu—, Pb— and U(VI)-citrate are presented in FIG. 2. The degradation of iron citrate complexes is shown in FIG. 3.

The results show the following:

Citric Acid. In FIG. 2, degradation of uncomplexed citrate is shown. Citrate was completely degraded in less than 15 h at a rate of 57 μmoles/h. The pH of the culture medium increased from 6.2 to 8.0. The increase in pH was due to the degradation of citric acid which resulted in the loss of buffering capacity of the medium.

Calcium citrate. Calcium citrate (1:1 complex) a simple bidentate complex was degraded in less than 13 h at a rate of 77.5 μmoles/h (FIG. 1). The rate of degradation of calcium citrate was much higher than the citrate alone.

Ferric iron citrate. Iron(III) citrate, a bidentate complex with iron partially hydrolyzed, was completely degraded by the bacteria in about 60 h at the rate of 16 μmoles/h (FIG. 2). However, the rate of Fe(III)-citrate degradation was slower than the uncomplexed citrate. The final pH of the culture medium was 7.4. The lower pH at the end of the experiment as compared to the uncomplexed citrate was due to hydrolysis of the released iron. After complete degradation of the iron citrate complex, iron was present as ferric hydroxide precipitate. This indicates that the bulk of the iron was removed from the complex and the citrate transported inside the cell and metabolized.

Ferrous iron citrate. Initially, little degradation of the tridentate iron(II) citrate complex was observed. As the pH of the growth medium increased due to slow citrate metabolism by the bacteria, the tridentate Fe(II) citrate complex was converted first to the tridentate FeOHCit$^-$ complex by oxidation and hydrolysis. FeOHCit$^-$ was biodegraded at the rate of 1 μmole/h. The FeOHCit$^-$ complex was further hydrolyzed leading to the formation of the Fe(OH)$_2$Cit$^{2-}$ bidentate complex (FIG. 3) which was rapidly degraded. The formation of the Fe(III) bidentate complex from Fe(II) citrate was monitored by spectrophotometric analysis between 200 and 400 nm and it confirmed that the complex was identical to the Fe(OH)$_2$Cit$^{2-}$ complex prepared from iron(III). The conversion to the Fe(OH)$_2$Cit$^{2-}$ complex took about 100 hours after which the complex was rapidly degraded in the same manner as the iron(III) citrate complex. The rate of degradation of these complexes was dependent upon the rate at which they were converted to the more hydrolyzed form of the Fe(III) complex. Bacteria accelerated the conversion of FeOHCit$^-$ to Fe(OH)$_2$Cit$^{2-}$ much more rapidly than the chemical oxidation and hydrolysis processes in the control sample.

Nickel citrate. Degradation of nickel citrate was observed after an initial lag period of 15 h. The rate of degradation was 8.6 /μmoles/h. 70% of the added nickel citrate was degraded by the bacteria (FIG. 2). The pH of the culture medium at the end of the incubation was 7.6. Nickel citrate at acid to near neutral pH existed as a bidentate complex of the form $NiCit^-$. At higher pH, nickel forms a tridentate complex. As the pH of the culture medium was increased due to bacterial metabolism of the citrate the alcoholic hydroxyl group was ionized leading to formation of the tridentate complex.

Lead citrate. Lead formed a number of different types of complexes with citrate which was apparent from the broad inflection points observed from the potentiometric titration data. At pH 6.2, lead was present predominantly as $PbCit^-$ and $PbCit_2^{4-}$ forms. These species have the alcoholic hydroxyl group of the citrate ion involved in the bonding of the metal. In the biodegradation of the 1:1 complex of lead citrate it was noted that about 20% of the citrate disappeared from solution during the first 10 hours of the experiment. The pH of the medium remained unchanged (6.2). The presence of a white precipitate of lead citrate was also evident in the flask. Analysis of the solution and the precipitate for both lead and citrate suggested that lead citrate complex was not biodegraded (FIG. 2).

Cadmium, copper and uranium citrate were not biodegraded under these conditions, but these metals could be removed using other aspects of the inventive process as shown below. Example 2 below shows that the addition of glucose to medium containing Cd—, Cu— and Pb— citrate complexes showed degradation of the complex (Table I) by the isolate of the invention.

EXAMPLE 2

Effect of Excess Citrate and Glucose on Biodegradation of Metal Citrate Complexes To determine whether the degradation of the metal citrate complex can be influenced by the metabolism of uncomplexed citrate or the addition of glucose and also to determine whether there was any toxicity associated with the metal-citrate complex on the bacteria, the following experiments were performed. Equimolar 1:1 metal citrate complexes consisting of $Cd^{2+}$, $Ni^{2+}$, $Pb^{2+}$, or $UO_2^{2+}$ were added to the medium containing 0.52 mM uncomplexed citrate. The degradation of citrate in medium containing the metal citrate complex was monitored in the presence of one-fold excess citrate. The treatment consisted of (i) 1.04 mM uncomplexed citrate only (control), (ii) 0.52 mM uncomplexed citrate plus 0.52 mM 1:1 metal citrate complex added at the start of the experiment, and (iii) 0.52 mM uncomplexed citrate followed by addition of 0.52 mM 1:1 metal citrate complex after the onset of growth of the bacteria usually about ten hours after addition of the inoculum. All three treatments in triplicate were inoculated with a 24 h old culture of the isolate and incubated in the dark at 26°±1° C. Sterile controls containing the metal complex were also included in the experiment. At periodic intervals, samples were taken for citrate, pH, and metal analysis.

Figure 4:
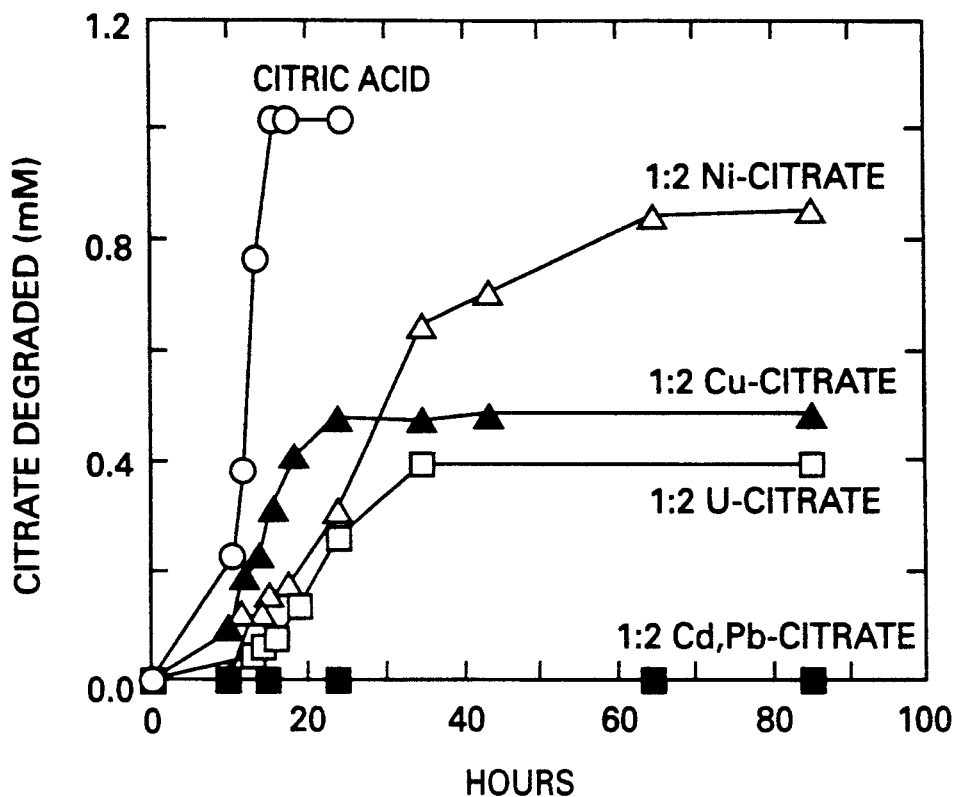
FIG. 4 is a graph of bacterial degradation of 1:2 metal citrate complexes.

In FIG. 4, the degradation of metal citrate complexes in the presence of excess citrate is shown. Degradation of the excess uncomplexed citrate was observed in samples which contained nickel citrate, copper citrate, or uranium citrate complex. Citrate degradation was not observed in samples containing cadmium or lead citrate complex because of polynuclear complex formation. These results also show that the metal citrate complexes studied were not toxic to bacteria. Lack of degradation is related to bacterial transport and/or metabolism of the complex.

Degradation of 1:1 metal citrate complexes of cadmium, copper, nickel, lead and uranium was tested in the presence of 0.52 mM glucose. The results are presented in Table I.

TABLE I

Degradation of Glucose and Citrate[a] in the Presence of Metal Citrate Complex

| Metal Complex | % Degradation | |
|---|---|---|
| | Glucose | Citrate[a] |
| No Metal | 100 (33)[b] | 100 (33) |
| Cd | 100 (82) | 35 |
| Cu | 100 (33) | 28 |
| Ni | 62 | 74 |
| Pb | 83 | 7 |
| U | 38 | 1 |

[a]Values are for a 107 hour incubation. Citrate and glucose are present at initial concentration of 0.52 mM.
[b]( ) = incubation time for complete degradation (hrs.)

Low biodegradation of uranium citrate complexes under these conditions was probably due to the formation of a 2:2 binuclear complex and a 2:3 complex in the presence of excess citrate and not due to toxicity. To verify this finding, the biodegradation of various ratios of uranium to citrate (Table II) was determined. In the presence of 0.25:1 and 0.50:1 uranium citrate complexes, the degradation of citric acid was 49% and 29%, respectively. However, with 0.75:1 complex, 8% of the complex was degraded. Also, a visible scan of the complex with a maximum absorbance at 438 nm showed that the 0.75:1 complex did not follow Beers Law in comparison to the other complexes. Therefore, it is likely that this complex is different than those that have been reported.

TABLE II

Degradation of Citrate in the Presence of Uranium-Citrate Complex

| Uranium: Citrate (Molar Ratio) | Citrate Degraded (%) | |
|---|---|---|
| | Predicted | Observed* |
| 0:1 | 100 | 100 |
| 0.25:1 | 75 | 49 |
| 0.50:1 | 50 | 29 |
| 0.75:1 | 25 | 8 |
| 1:1 | 0 | 0 |

*The differences between predicted and observed values for 0.25, 0.5, and 0.75:1 complexes are probably due to formation of a 2:3 complex.

Biodegradation Versus Formation Constant of Metal Citrate Complex

The logK of the metal citrate complexes are listed in Table III. If formation constant of the complex was a factor in the biodegradation, the ease with which bacteria could degrade the complex should follow the order $Fe(II)(OH)_2 > Ca > Cd > Pb > Fe(II) > Ni > Cu > U(VI) > Fe(III)OH$. Results showed that the bacteria degraded the metal citrate complexes in the following order: $Ca > Fe(III)OH_2 > Ni > Fe(III)OH$. Degradation of Fe(II), Cu, Cd, Pb, or U(VI) was not observed. These results suggest that the structure of the complex rather than the stability play an important role in determining the biodegradation of the complexes.

TABLE III

Biodegradation of Metal-Citrate Complexes

| Type of Complex | Metal | Formula | Formation Constant (log K) | Biodegradation % | Rate ($\mu$ moles/h) |
|---|---|---|---|---|---|
| Bidentate | Calcium | $CaCit^-$ | 3.5 | 100 | 77 |
| | Nickel | $NiCit^-$ | 5.4 | 70 | 9 |
| | $Fe^{3+}$ | $Fe(OH)_2Cit^{2-}$ | 1.9–2.6 | 100 | 16 |
| Tridentate | $Fe^{3+}$ | $Fe(OH)Cit^-$ | 9.4 | 16 | 1 |
| | $Fe^{2+}$ | $FeCit^-$ | 4.4 | 0 | 0 |
| | Copper | $CuCit^{2-}$ | 5.9 | 0 | 0 |
| | Cadmium | $CdCit^-$ | 3.8 | 0 | 0 |
| | Lead | $PbCit^-$ | 4.1 | 0 | 0 |
| Binuclear | Uranium | $(UO_2)_2(Cit)_2^{4-}$ | 18.9 | 0 | 0 |

EXAMPLE 3

Photochemical Degradation of Uranium Citrate Complex

Figure 5:
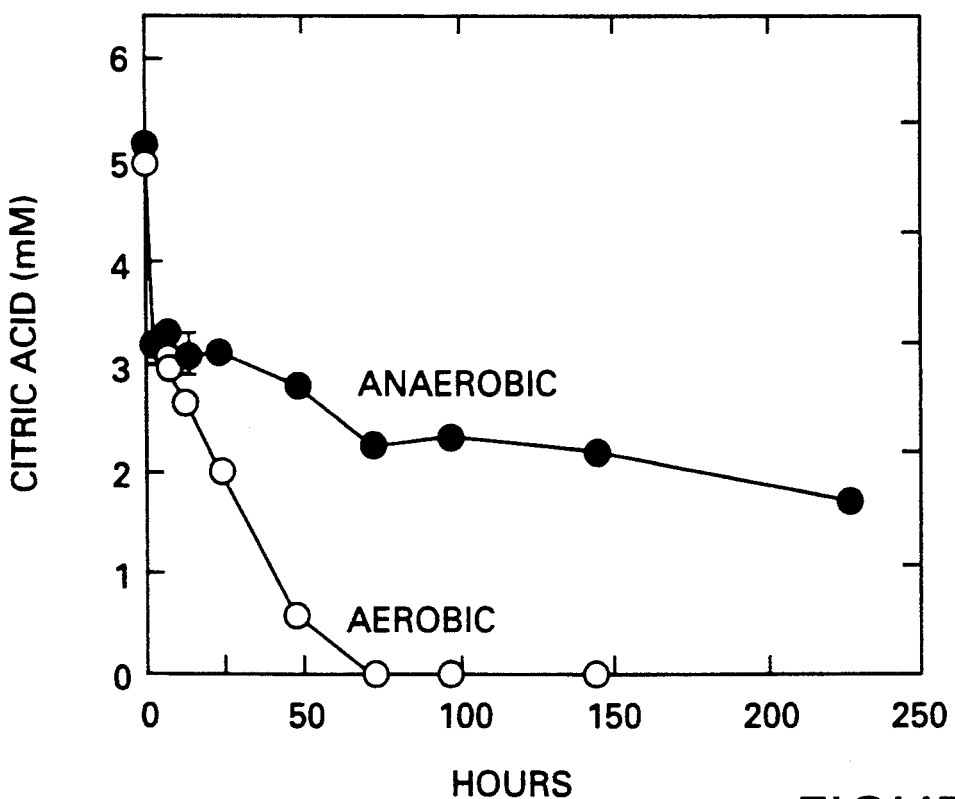
FIG. 5 is a graph of the photochemical degradation of citrate from 1:1 uranium citrate complex under aerobic and anaerobic conditions.
Figure 6:
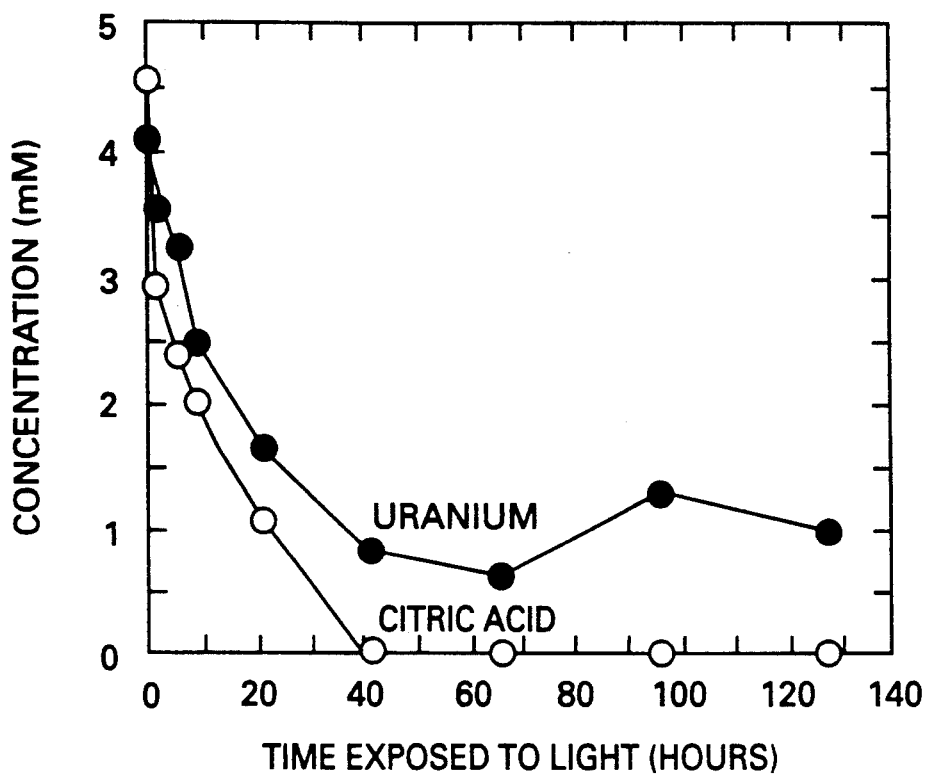
FIG. 6 is a graph of the photochemical degradation of uranium citrate complex under aerobic conditions showing citrate degradation and uranium precipitation.

A 5.0 mM 1:1 uranium:citrate complex was prepared by combining equimolar amounts of citric acid and uranyl nitrate in deionized water. The pH of the sample was adjusted to 6.0 with 1N NAOH and the ionic strength to 0.1M with KCl. One hundred milliliters of the sample was transferred to 125 ml acid washed serum bottles and was incubated under 60 watt high output growth lights (Westinghouse, cool white #F24T12) at 25° C. Aerobic sample bottles were fitted with cotton plugs whereas the anaerobic samples were purged with nitrogen for about 20 minutes and then fitted with butyl rubber stoppers. Control samples were incubated in the dark. At periodic intervals samples were withdrawn and analyzed for pH, uranium and citric acid and its degradation products. Citric acid degradation products were identified by GC/MS. Under aerobic and anaerobic conditions, U(VI) citrate (aqueous) was photodegraded to yield a precipitate of U(VI) and citrate degradation products of acetic acid and $CP_2$. Minor amounts of intermediate degradation products of citrate such as 3-oxoglutaric acid and a few unidentified products were also observed. Photodegradation of 1:1 uranium citrate complex under aerobic and anaerobic conditions is shown in FIG. 5. Photodegradation of uranium citrate complex was much more rapid and complete under aerobic conditions than under anaerobic conditions. Photodegradation of 1:1 uranium citrate complex showing the fate of uranium under aerobic conditions is presented in FIG. 6.

EXAMPLES 4–6

In the following examples, sediments and sludge samples containing uranium and toxic metals were extracted according to the method of the invention, using a batch reactor process. The quantity of extracted metals was determined and compared to the total metal in the waste before extraction to determine the extraction efficiency of the process. Other process parameters studied included contact time of citric acid with the waste, and mass reduction of the waste as a result of the extraction.

EXAMPLE 4

Figure 7:
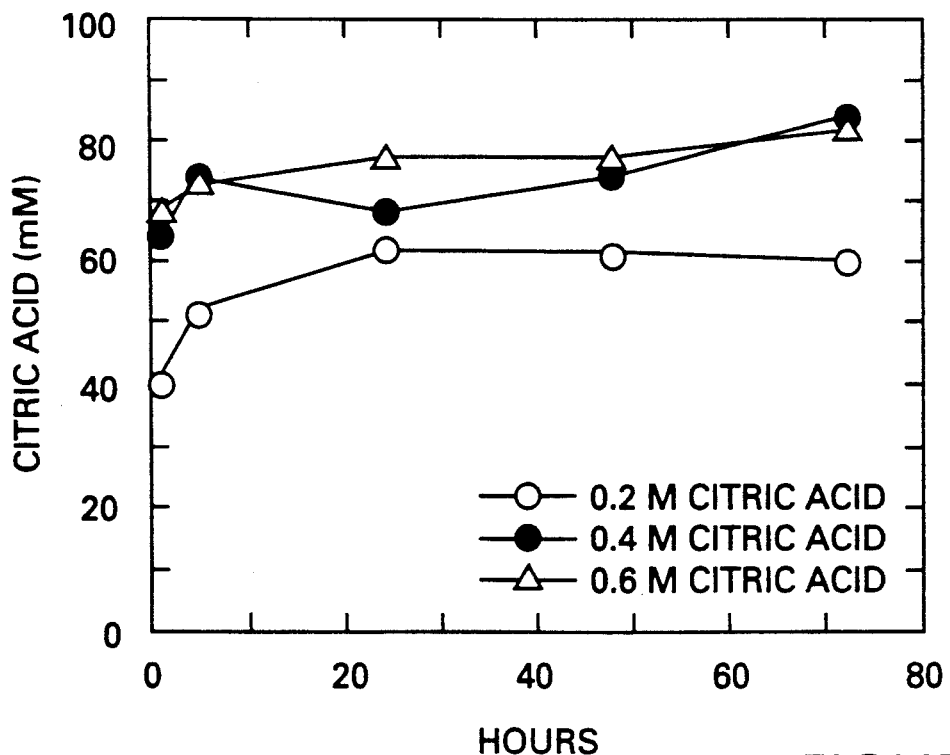
FIG. 7 is a graph of extraction of uranium from sludge using different concentrations of citric acid.

Comprehensive Method for Extraction of Radionuclides and Metals from Sludge A sludge sample containing uranium and several toxic metals was obtained from a uranium processing facility. This sample also contained a large amount of calcium carbonate due to waste processing. Ten grams of sludge was extracted with 100 ml of: 1) deionized water, ii) 0.20M citric acid, iii) 0.40M citric acid, and iv) 0.60M citric acid. Duplicate samples of each was mixed well on a wrist action shaker in the dark. The samples were centrifuged for ten minutes at 7000 rpm and 10 ml aliquots were removed at 0, 5, 24, 48, and 72 hours, filtered through a 0.22 $\mu$m filter and analyzed for uranium by a spectrophotometric method. The results presented in FIG. 7 show that 75% of the uranium was extracted using 0.4M citric acid in five hours and that there was little gained by using more concentrated citric acid or longer extraction times. Subsequent extractions of metals from sludge were performed by treating with 0.40M citric acid for 5 hours. The extraction efficiency of several metals by 0.40M citric acid treated for 5 hours was determined by analyzing the metals in the extract and in the remaining solids. The dry weight of the solids before and after citric acid extraction was also determined by drying at 60° C. until a constant weight was obtained. The solids were digested in a mixture of hot nitric, perchloric and hydrofluoric acids in platinum crucibles. Uranium and metals in the citric acid extract and digested solids were analyzed by ICP-MS. Uranium was also analyzed by spectrophotometric method. The extraction efficiency of various metals from sludge by 0.40M citric acid treated for 5 hours is shown in Table IV.

TABLE IV

Extraction Efficiency of Metals from Sludge by Citric Acid

| | Before Treatment ug·gdw$^{-1}$ | After Treatment ug·gdw$^{-1}$ | Extraction Efficiency |
|---|---|---|---|
| Ag | 41 ± 30 | 40 ± 30 | 2.4 |
| Al | 30500 ± 500 | 12600 ± 300 | 58.7 |
| Au | 1800 ± 500 | 1800 ± 500 | <1 |
| Ba | 427 ± 25 | 323 ± 9 | 24.4 |
| Be | 5.21 ± .45 | 2.08 ± 0.39 | 60.1 |
| Bi | 54 ± 7 | 53 ± 7 | 1.9 |
| Cd | 66 ± 6 | 60 ± 6 | 9.1 |
| Co | 10.7 ± 0.3 | 2.7 ± 0.1 | 74.8 |
| Cr | 342 ± 10 | 87 ± 7 | 74.6 |
| Cu | 329 ± 18 | 325 ± 18 | 1.2 |
| Ga | 28.8 ± 0.6 | 21.4 ± 0.6 | 25.7 |
| Hf | 5.68 ± 0.17 | 1.30 ± 0.52 | 77.1 |
| La | 40.7 ± 1.0 | 36.9 ± 0.8 | 11.5 |
| Mg | 7510 ± 100 | 810 ± 110 | 89.2 |
| Mn | 234 ± 3 | 40 ± 2 | 82.9 |
| Nb | 23.7 ± 0.6 | 13.1 ± 0.6 | 44.7 |
| Ni | 1120 ± 10 | 224 ± 6 | 80.0 |
| Pb | 224 ± 27 | 222 ± 30 | <1 |
| Pd | 5.51 ± 0.70 | 2.81 ± 0.73 | 49.0 |
| Sb | 5.67 ± 0.05 | 1.77 ± 0.03 | 68.8 |
| Sc | 1.73 ± 0.45 | 0.57 ± 0.40 | 67.1 |
| Sn | 17.6 ± 0.4 | 1.21 ± 0.05 | 93.1 |
| Sr | 125 ± 5 | 51 ± 3 | 59.2 |

TABLE IV-continued

Extraction Efficiency of Metals from Sludge by Citric Acid

| | ug · gdw$^{-1}$ | | |
|---|---|---|---|
| | Before Treatment | After Treatment | Extraction Efficiency |
| Ta | 6.96 ± 0.50 | 3.83 ± 0.54 | 45.0 |
| Th | 3.08 ± 0.10 | 0.18 ± 0.08 | 94.2 |
| Ti | 922 ± 95 | 660 ± 83 | 28.4 |
| Tm | 1.90 ± 0.05 | 0.84 ± 0.04 | 55.8 |
| U | 2410 ± 100 | 317 ± 33 | 86.8 |
| V | 121 ± 7 | 116 ± 6 | 4.1 |
| Zn | 839 ± 7 | 339 ± 7 | 59.6 |
| Zr | 209 ± 4 | 33 ± 6 | 84.2 |

Sludge extracted for 5 hours with 0.4M citric acid solution.

In this particular sample, metals Ag, As, Au, B, Bi, Cu, Gd, Hg, Li, Mo, Pb, Tb, and V were not extracted by citric acid treatment. Lack of extraction of these metals is probably due to the nature of mineralogical association with stable mineral phases in this particular waste. Each type of waste sample is expected to vary in this respect. However, the method of the invention is capable of removing all metals.

Differences in the amounts of the metals extracted from the sludge and sediment by citric acid depends in part on the extent and nature of association of metals with various mineral phases such as exchangeable, carbonate, iron oxide and organic fractions. Mineralogical associations are discussed in U.S. Pat. No. 5,047,152 which is herein incorporated by reference.

Biodegradation of Citric Acid Sludge Extract

Figure 8:
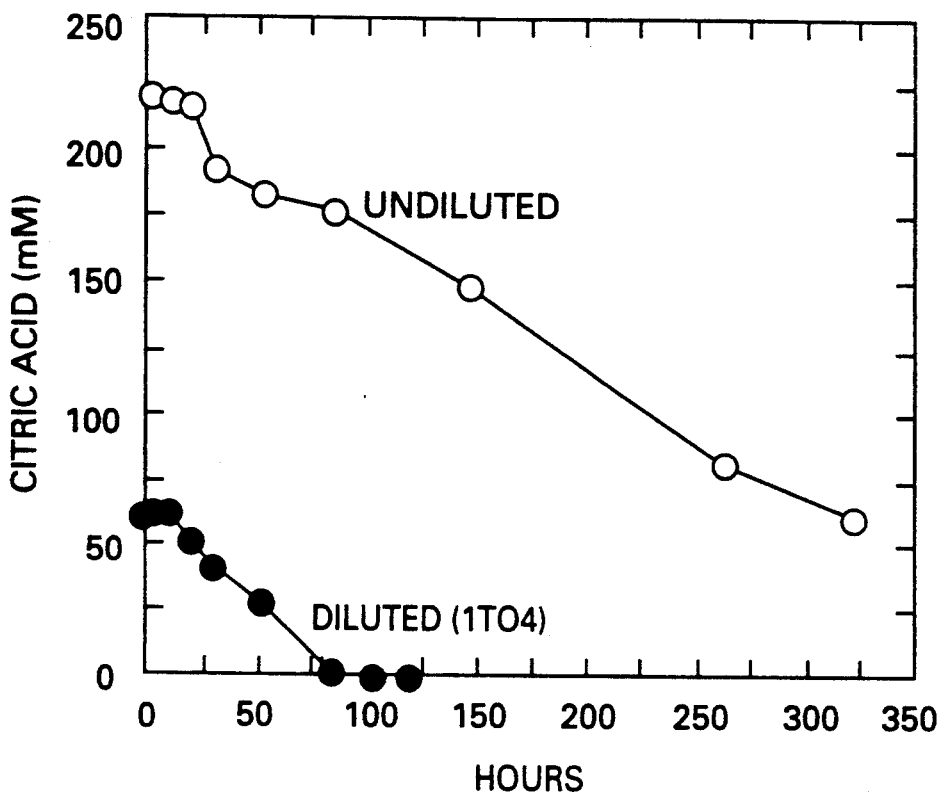
FIG. 8 is a graph of biodegradation of citrate in diluted and undiluted citric acid sludge extract.
Figure 9:
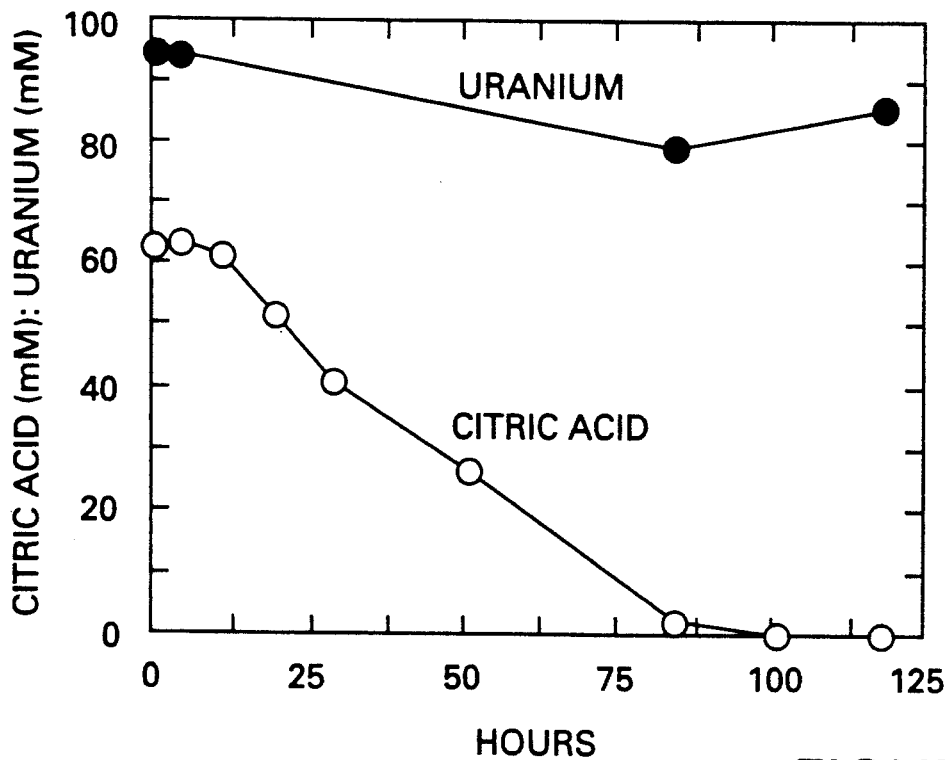
FIG. 9 is a graph of biodegradation of citrate in sludge citric acid extract depicting the fate of uranium.

Duplicate samples of undiluted (as is) and diluted (1 to 4) citric acid extract from the sludge were amended with nutrients consisting of 0.1% of $NH_4Cl$, $K_2HPO_4$ and $KH_2PO_4$. The pH was adjusted to 6.5 with NAOH and then the extracts (100 ml) were inoculated with 4 ml of 18 hour old culture of Pseudomonas fluorescens ATCC 55241. The samples were incubated on a shaker at 24° C. The bacterial inoculum was grown in medium containing citric acid, 2 g; $NH_4Cl$, 1 g; $KH_2PO_4$ 1 g; $K_2HPO_4$, 1 g; NaCl, 4 g, $MgSO_4$, 0.2 g; distilled water 1000 ml, and pH 6.5. All sample preparations were performed under low light to minimize any photochemical reactions. Periodically, 5 ml aliquots were removed, filtered through a 0.22 μm filter, and analyzed for (i) pH, (ii) citric acid biodegradation by HPLC using uv and refractive index detectors and (iii) uranium. At the end of the incubation period (after 118 hours for the diluted sample and after 322 hours for undiluted sample) the supernatant and the solids consisting of bacterial biomass and any precipitated metals were separated from solution by centrifugation. The dry weight of the solids was determined and digested in a hot mixture of nitric and perchloric acids. The supernate and the digested solids were analyzed for uranium and other metals by ICP-MS. The results are presented in Table V below. The bacteria degraded citrate at a rate of 0.5–0.7 mM per hour. The rate of degradation was much higher in the diluted extract than the undiluted sample (FIG. 8). There was little change in concentration of uranium in samples subjected to biodegradation (FIG. 9), indicating that the uranium citrate complex was not biodegraded. This is consistent with the finding that uranium and certain metals complexes of citric acid are resistant to biodegradation. There was, however, a small decrease in uranium concentration in solution and some uranium (about 10% of what was in the sludge originally) was present in the bacterial biomass (data not shown). The levels of cobalt, nickel, zinc and zirconium, were higher in the biomass digest, indicating that their citrate complexes are readily biodegraded.

Photodegradation of Uranyl:Citrate Complex

Figure 10:
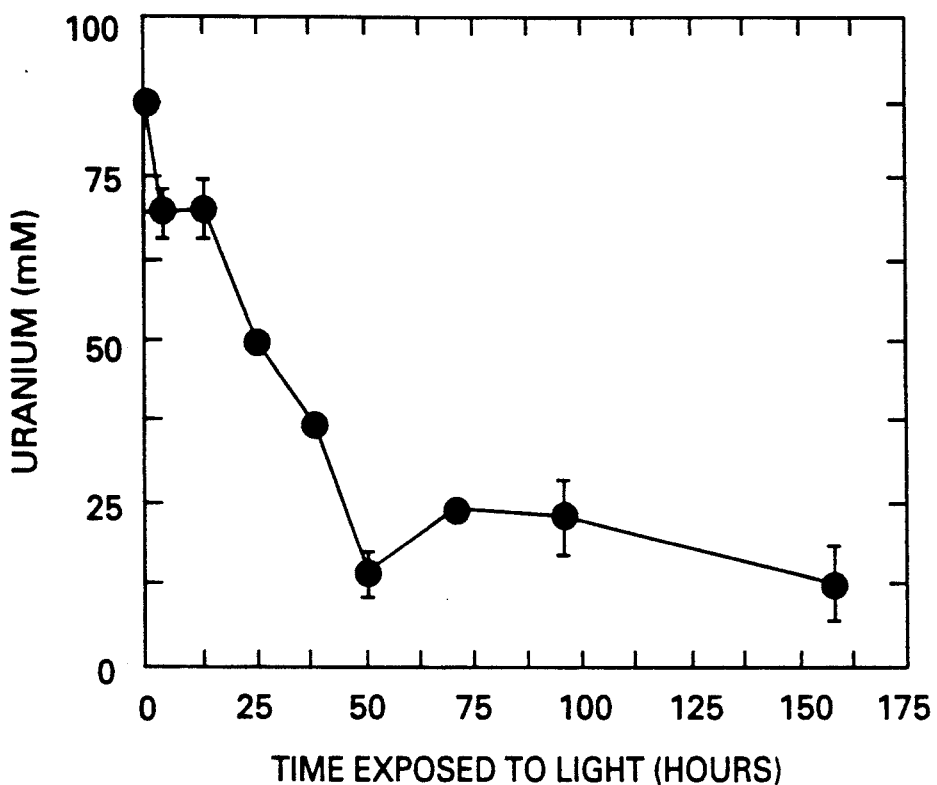
FIG. 10 is a graph of photodegradation of uranium citrate complex after biodegradation of citrate in the sludge citric acid extract.

The supernate from the biodegradation treatment containing primarily uranium citrate complex was exposed to light to degrade the complex and recover uranium. The pH of the supernate was adjusted to 3.5 with HCl and the sample was exposed to seven 60 watt high output fluorescent growth lights. Periodically 2 ml samples were withdrawn, filtered through a 0.22 μm filter and analyzed for uranium, citric acid and photodegradation products. At the end of the experiment (after 157 hours of exposure to light) the solutions were filtered through a 0.22 μm Millipore filter and analyzed for citric acid degradation products by HPLC, and uranium and other metals by ICP-MS. The results in FIG. 10 show that the uranium precipitated out of solution as a polymer soon after it was exposed to light. After 50 hours, ~85% of the uranium was removed from solution.

In Table V, the removal efficiency of various metals from the citric acid sludge extract first subjected to biodegradation followed by photodegradation is presented.

TABLE V

Effects of Biodegradation Followed by Photodegradation in the Treatment of Citric Acid Sludge Extract

| | uM | | | Overall Removal Efficiency (%) |
|---|---|---|---|---|
| Metal | Before Treatment[1] | After Biodegradation[2] | After Photochemistry[3] | |
| Al | 7410 | 624 ± 212 | 501 ± 44 | 93.2 |
| Ba | 12.0 | 0.574 ± 0.139 | 0.978 ± 0.416 | 91.9 |
| Be | 3.22 | ND | ND | >99 |
| Co | 0.866 | 0.255 ± .051 | 0.204 ± 0.068 | 76.5 |
| Cr | 60.8 | 60.6 ± 2.50 | 45.8 ± 1.73 | 24.7 |
| Ga | 0.889 | 0.244 ± 0.014 | 0.100 ± 0.029 | 88.7 |
| Hf | 0.230 | ND | ND | >99 |
| Mn | 37.2 | 0.656 ± 0.164 | 0.856 ± 0.255 | 97.7 |
| Nb | 1.17 | 0.527 ± 0.054 | 0.086 ± 0.000 | 92.7 |
| Ni | 192 | 68.8 ± 3.4 | 66.8 ± 4.43 | 65.3 |
| Pd | 0.311 | 0.113 ± 0.057 | 0.019 ± 0.000 | 93.9 |
| Sb | 0.361 | 0.352 ± 0.008 | 0.303 ± 0.025 | 15.9 |
| Sc | 0.311 | 0.378 ± 0.044 | 0.067 ± 0.000 | 78.6 |
| Sn | 1.71 | ND | ND | >99 |
| Sr | 10.2 | 0.160 ± 0.023 | 0.148 ± 0.023 | 98.5 |
| Ta | 0.171 | 0.017 ± 0.006 | 0.006 ± 0.000 | 96.8 |
| Th | 0.112 | 0.004 ± 0.004 | ND | >99 |
| Ti | 80.2 | 2.96 ± 0.21 | 3.34 ± 0.42 | 95.8 |
| Tm | 0.243 | 0.006 ± 0.000 | ND | >99 |
| U | 94.8 | 85.9 ± 0.2 | 12.8 ± 5.5 | 86.5 |
| Zn | 86.1 | 8.50 | 4.25 ± 1.19 | 95.1 |
| Zr | 61.7 | 1.81 ± 0.077 | 0.318 ± 0.055 | 99.5 |

[1]Sludge was extracted for five hours with 0.4 M citric acid.
[2]Samples analyzed 118 hours after inoculaion with Pseudomonas fluorescens (ATCC No. 55241) but before photodegradation.
[3]Samples analyzed after biodegradation and 157 hours of exposure to light.
ND = None Detected These results show that (i) uranium was extracted from the waste sample with >85% efficiency using 0.4M citric acid, (ii) other metals such as chromium, cobalt, manganese, nickel, strontium, thorium, zinc and zirconium, were are also extracted from the waste; (iii) the uncomplexed excess citrate and several metal citrate complexes with the exception of binuclear complexes were readily biodegraded by the bacterium P. fluorescens ATCC 55241, (iv) metal citrates which were biodegradable i.e., cobalt, nickel, zinc and zirconium were recovered with the bacterial biomass; (v) the uranium citrate complex was photodegraded, allowing the uranium to form a polymer which was recovered as a concentrated solid.

EXAMPLE 5

Sediment

Ten grams of contaminated sediment sample also obtained from a uranium processing facility was extracted with 100 ml of the following solutions: (i) deionized water, (ii) 0.05M citric acid, (iii) 0.10M citric acid, and (iv) 0.20M citric acid. Aliquots of the extract were taken at 1 h, 6 h, 24 h, and 48 h, centrifuged and filtered through a 0.22 μm filter and analyzed for uranium. The dry weight of the remaining solids after the citric acid extraction was also determined. The extraction efficiency of uranium by various concentrations of citric acid are presented in Table VI.

TABLE VI

| Extraction of Uranium From Sediment by Citric Acid | | | | |
|---|---|---|---|---|
| Citric acid Concentration | Uranium extracted (%) Extraction Time (Hours) | | | |
| | 1 | 6 | 24 | 48 |
| 0.0 M | ND | ND | ND | ND |
| 0.05 M | 12.7 | 17.7 | 20.6 | 23.8 |
| 0.1 M | 20.0 | 24.7 | 29.7 | 33.3 |
| 0.2 M | 20.9 | 26.6 | 30.8 | 33.0 |

ND = None Detected.

Figure 11:
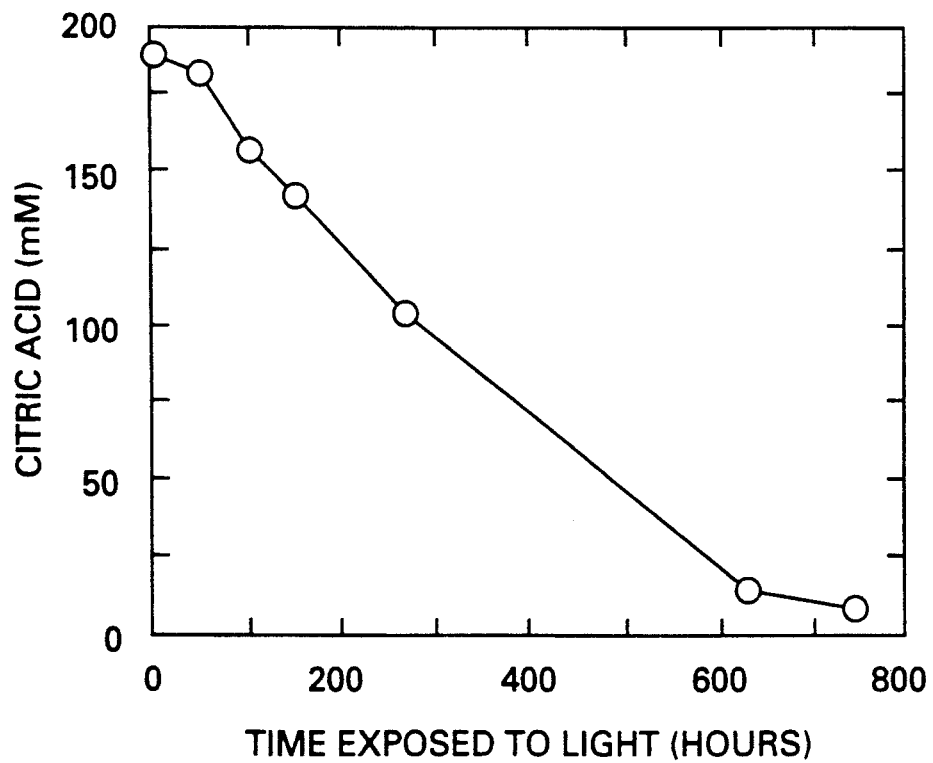
FIG. 11 is a graph of photodegradation of citrate in citric acid sediment extract.

About 33% of uranium in the sediment was extracted by 0.1M or 0.2M citric acid treated for 48 h. Substantial amounts of cadmium, chromium, manganese, nickel, and zinc were also extracted (data not shown). The 0.2M citric acid extract of sediment was subjected to photodegradation. The results of this photodegradation graphed in FIG. 11 show rapid photolytic degradation of citrate.

EXAMPLE 6

Weight Loss. The solids remaining after extraction with citric acid from Examples 5 and 6 were washed with deionized water, were transferred to weighing dishes and dried in an oven overnight at 105° C. to determine the weight loss due to citric acid extraction.

The extraction of the wastes with citric acid resulted in significant reduction in weight. Almost half (47%) of the sludge and 23% of the sediment showed loss in weight due to solubilization and removal of toxic and nontoxic bulk components in the waste. The results are given in Table VII.

TABLE VII

| Mass Reduction of Wastes Due to Citric Acid Extraction | | | |
|---|---|---|---|
| Waste | Weight Before Extraction (g) | Weight After Extraction (g) | Mass Reduction (%) |
| Sludge | 4.41 ± 0.05 | 2.32 ± 0.10 | 47 ± 3 |
| Sediment | 4.24 ± 0.07 | 3.27 ± 0.06 | 23 ± 1 |

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A method for decontamination and reclamation of materials contaminated with radionuclides, metals, or mixtures thereof comprising:

(i) contacting the material with an organic complexing agent comprising citric acid, a citrate salt or mixture thereof in an aqueous solution to remove said radionuclides, metals or mixtures thereof from the material and yield a radionuclide and/or metal-citrate complex-containing solution;

(ii) treating the radionuclide and/or metal-citrate complex-containing solution with a bacterial culture containing *Pseudomonas fluorescens* ATCC No. 55241 wherein a nutrient carbon source for the bacteria consists substantially of citrate in the form of the radionuclide and/or metal-citrate complexes, said treatment resulting in the precipitation or incorporation into biomass of the radionuclides and/or metals; and (iii) if the material being decontaminated and reclamated contains the radionuclide uranium, exposing the uranium citrate complex-containing solution to light resulting in the breakdown of the complex and precipitation of uranium as a polymer; so that the radionuclides and/or metals are recovered in a concentrated form.

2. The method of claim 1 wherein the material is selected from a group consisting of soil, sediment, sludge and aquatic environments.

3. The method of claim 1 wherein the step (ii) treating is at a temperature of from about 18° C. to about 32° C., at an initial pH of from about 4 to about 8.

4. The method of claim 1 wherein citric acid, a citrate salt or mixture thereof is added in a concentration in excess of the concentration of the radionuclides and/or metals in the contaminated material.

5. The method of claim 1 wherein the concentration of the citric acid, citrate salt or mixture thereof is from about 0.01M to about 1.0M.

6. The method of claim 1 further comprising adding a supplemental carbon source in step (ii).

7. The method of claim 6 wherein the supplemental carbon source is glucose.

8. The method of claim 1 wherein the solution in step (iii) has an initial pH of from about 2 to about 8, and is exposed to daylight for a time of at least 12 hours.

9. The method of claim 1 further comprising adding supplemental photoreactive compound to the solution of step (iii).

10. The method of claim 9 wherein the photoreactive compound is ferric iron.

11. The method of claim 1 wherein the solution in step (iii) is exposed to sunlight.

12. The method of claim 1 wherein step (ii) is carried out after step (iii).

13. The method of claim 1 wherein step (ii) is carried out concurrently with step (iii).

* * * * *